United States Patent [19]

Seele et al.

[11] Patent Number: 5,057,531

[45] Date of Patent: Oct. 15, 1991

[54] AZOLYLMETHYLOXIRANES AND FUNGICIDES CONTAINING THESE COMPOUNDS

[75] Inventors: Rainer Seele, Fussgoenheim; Stefan Karbach, Neustadt; Norbert Goetz, Worms; Gisela Lorenz, Neustadt; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 314,963

[22] Filed: Feb. 24, 1989

[30] Foreign Application Priority Data

Feb. 26, 1988 [DE] Fed. Rep. of Germany ....... 3806089

[51] Int. Cl.$^5$ ................ A01N 43/647; C07D 249/08
[52] U.S. Cl. .................... 514/383; 514/184; 548/267.8; 548/268.6; 548/268.8; 548/101
[58] Field of Search .............. 548/101, 262, 267.8, 548/268.6, 268.8; 514/184, 383

[56] References Cited

U.S. PATENT DOCUMENTS

| | | | |
|---|---|---|---|
| 4,057,545 | 11/1977 | Gutsche et al. | 548/335 |
| 4,104,399 | 8/1978 | Pommer et al. | 548/262 |
| 4,282,238 | 8/1981 | Goetz et al. | 548/335 |
| 4,464,381 | 8/1984 | Janssen et al. | 514/383 |
| 4,625,036 | 11/1986 | Boyle | 548/262 |
| 4,652,580 | 3/1987 | Janssen et al. | 514/383 |
| 4,780,471 | 10/1988 | Maeda et al. | 514/383 |

FOREIGN PATENT DOCUMENTS

| | | | |
|---|---|---|---|
| 1204117 | 5/1982 | Canada . | |
| 061835 | 10/1982 | European Pat. Off. | 548/262 |
| 0150892 | 1/1985 | European Pat. Off. . | |
| 196038 | 10/1986 | European Pat. Off. | 548/262 |

OTHER PUBLICATIONS

Chemical Abstracts, vol. 93, 1–Pharmacodynamics No. 23, 215,969 d (1980).
Chemical Abstracts, vol. 99, 1–Pharmacology No. 23, 194,892 e (1983).

*Primary Examiner*—Patricia L. Morris
*Attorney, Agent, or Firm*—Oblon, Spivak, McClelland, Maier & Neustadt

[57] ABSTRACT

Azolylmethyloxiranes of the general formula I

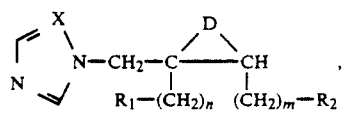

where
$R_1$ and $R_2$ are substituted or unsubstituted alkyl, naphthyl, biphenyl, dioxanyl or phenyl,
m and n are each an integer from 1 to 5 or 0, with the proviso that m+n is 1 or more, D is oxygen or a single bond,
X is CH or N, and their plant-tolerated acid addition salts and metal complexes, and fungicides containing these compounds.

10 Claims, No Drawings

AZOLYLMETHYLOXIRANES AND FUNGICIDES CONTAINING THESE COMPOUNDS

The present invention relates to novel azole compounds, processes for their preparation and fungicides containing these compounds, and methods for controlling fungi with these compounds.

It is known that 2-(1,2,4-triazol-1-ylmethyl)-2-(tert-butyl)-3-(4-chlorophenyl)-oxirane can be used as a fungicide (DE-3 218 130.2). However, its action is inadequate.

We have found that azolylmethyloxiranes of the general formula I

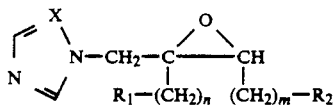

where $R_1$ and $R_2$ are each $C_1$-$C_5$-alkyl, naphthyl, biphenyl, dioxanyl or phenyl, these radicals being unsubstituted or substituted by halogen, nitro, phenoxy, alkyl, alkoxy, amino or haloalkyl where each alkyl radical is of 1 to 4 carbon atoms, m and n are each an integer of from 1 to 5 or 0, with the proviso that the sum m+n is 1 or greater than 1, D is O or a single bond and X is CH or N, or their plant-tolerated acid addition salts or metal complexes have a better fungicidal action, in particular against cereal diseases, than the known azole compounds.

The compounds of the known formula I contain chiral centers and are generally obtained in the form of racemates or as diastereomer mixtures of erythro or threo forms. In the case of the novel compounds, the erythro or threo diastereomers can be separated in a conventional manner, for example on the basis of their different solubilities or by column chromatography, and can be isolated in pure form. Pure enantiomers can be obtained from such an isolated diastereomer by a conventional method. Both the pure diastereomers or enantiomers and their mixtures obtained in the synthesis can be used as fungicides. The present invention embraces all these compounds.

$R_1$ and $R_2$ are each, for example, methyl, ethyl, isopropyl, n-propyl, n-butyl, sec-butyl, tert-butyl, n-pentyl, neopentyl, 1-naphthyl, 2-naphthyl, p-biphenyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, alkoxyphenyl, 2-methoxyphenyl, 3-methoxyphenyl, 4-methoxyphenyl, 2,4-dimethoxyphenyl, alkylphenyl, 4-ethylphenyl, 4-isopropylphenyl, 4-tert-butylphenyl, 4-tertbutoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl, 4-trifluoromethylphenyl, 1,3-dioxan-2-yl, cyclohexyl, cyclopentyl, cyclopropyl, cycloheptyl or 1,4-dioxan-1-yl.

Acid addition salts are, for example, the hydrochlorides, bromides, sulfates, nitrates, phosphates, oxalates or dodecylbenzenesulfonates. The activity of the salts is due to the cation, so that in general any anion may be chosen. The novel active ingredient salts are prepared by reacting the azolylmethyloxirane with the acid.

Metal complexes of the active ingredients or their salts can be formed with copper, zinc, tin, manganese, iron, cobalt or nickel by reacting the azolylmethyloxirane with the corresponding metal salt, for example with copper sulfate, zinc chloride, tin chloride, manganese sulfate, iron chloride or cobalt sulfate.

The compounds of the formula I can be prepared, for example, by a) reacting a compound of the formula II

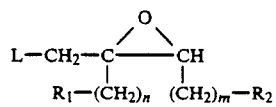

where $R_1$, $R_2$, D, m and n have the abovementioned meanings and L is a leaving group which can be nucleophilically substituted (OH or halogen), with a compound of the formula III

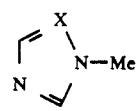

where Me is hydrogen or a metal atom (Na or K) and X has the abovementioned meanings, or b) converting a compound of the formula IV

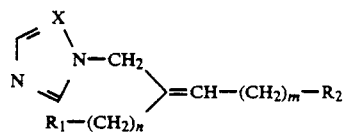

where $R_1$, $R_2$, m, n and X have the abovementioned meanings, into the epoxide.

Where Me is hydrogen, reaction a) is carried out in the presence or absence of a solvent or diluent, with or without the addition of an inorganic or organic base and of a reaction accelerator, at from 10° to 120° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane and mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate or cesium carbonate, and sodium bicarbonate, potassium bicarbonate and cesium bicarbonate, and pyridine and 4-dimethylaminopyridine. However, other conventional bases can also be used.

Preferred reaction accelerators are metal halides, such as sodium iodide or potassium iodide, quaternary ammonium salts, such as tetrabutylammonium chloride, bromide, iodide or bisulfate or benzyltriethylammonium chloride or bromide and crown ethers, such as 12-crown-4, 15-crown-5, 18-crown-6, dibenzo-18-crown-6 or dicyclohexano-18-crown-6.

The reaction is carried out in general at from 20° to 150° C., under atmospheric or superatmospheric pressure, continuously or batchwise.

Where Me is a metal atom (Na or K), reaction a) is carried out in the presence or absence of a solvent or diluent and with or without the addition of a strong inorganic or organic base, at from −10° to 120° C. The preferred solvents and diluents include amides, such as dimethylformamide, diethylformamide, dimethylacetamide, diethylacetamide, N-methylpyrrolidone or hexamethylphosphorotriamide, and sulfoxides, such as dimethyl sulfoxide or sulfolane.

Examples of suitable bases, which may also be used as acid acceptors in the reaction, are alkali metal hydrides, such as lithium hydride, sodium hydride and potassium hydride, alkali metal amides, such as sodium amide and potassium amide, and furthermore sodium tertbutoxide, potassium tert-butoxide, triphenylmethyllithium, triphenylmethylsodium, triphenylmethylpotassium, naphthalenelithium, naphthalenesodium and naphthalenepotassium.

Suitable diluents for reaction b) are polar organic solvents, such as nitriles, e.g. acetonitrile, sulfoxides, e.g. dimethylsulfoxide, formamides, e.g. dimethylformamide, ketones, e.g. acetone, ethers, e.g. diethyl ether or tetrahydrofuran, and in particular chlorohydrocarbons, e.g. methylene chloride or chloroform.

The reaction is carried out in general at from 0° to 100° C., preferably from 20° to 80° C. In the presence of a solvent, it is advantageously carried out at the boiling point of the particular solvent.

The novel starting compounds II are obtained by epoxidation of the corresponding olefins V

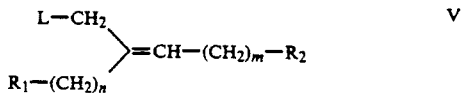

(cf. G. Dittus in Houben-Weyl-Müller, Methoden der Organischen Chemie, Georg Thieme Verlag, Stuttgart, 1965, Vol. VI, 3, page 385 et seq.).

Compounds V are prepared by halogenating or oxidizing an olefin of the formula VI

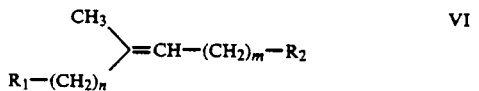

in the allyl position by a known method.

Suitable halogenating reagents are N-chloro- and N-bromosuccinimide in halohydrocarbons, such as carbon tetrachloride, trichloroethane or methylene chloride, at from 20° to 100° C. Allyl oxidation is carried out using peresters, such as tert-butyl perbenzoate or tert-butyl peracetate, in the presence of a heavy metal salt, such as copper(I) chloride or copper(I) bromide. The reaction is carried out in an inert solvent at from 10° to 100° C.

The resulting allyl halides or alcohols V are then converted into the corresponding epoxides II (where L is halogen or OH). For this purpose, the olefins V are oxidized with peroxycarboxylic acids, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, e.g. methylene chloride, chloroform, carbon tetrachloride or dichloroethane, and, if required, in acetic acid, ethyl acetate, acetone or dimethylformamide, in the presence or absence of a buffer, such as sodium acetate, sodium carbonate, disodium hydrogen phosphate or Triton B. The reaction is carried out at from 10° to 100° C. and, if necessary, is catalyzed, for example with iodine, sodium tungstate or light. The oxidation can also be carried out using alkaline solutions of hydrogen peroxide (about 30% strength) in methanol, ethanol, acetone or acetonitrile at from 25° to 30° C. and alkyl hydroperoxides, e.g. tert-butyl hydroperoxide, with the addition of a catalyst, e.g. sodium tungstate, pertungstic acid, molybdenum hexacarbonyl or vanadyl acetylacetonate. Some of the stated oxidizing agents can be produced in situ.

While the resulting epoxyhalides II (where L is halogen) in process a) can be converted immediately, the corresponding epoxyalcohols II (where L is OH) are converted into reactive esters, which are then reacted with the compounds III according to process a).

The reactive esters which are reacted with III are prepared by generally known methods (Houben-Weyl-Müller, Methoden der organischen Chemie, Georg Thieme Verlag, Stuttgart, 1955, Volume 9, pages 388, 663 and 671). Examples of such esters are methanesulfonates, trifluoromethanesulfonates, 2,2,2-trifluoroethanesulfonates, nonafluorobutanesulfonates, 4-methylbenzenesulfonates, 4-bromobenzenesulfonates, 4-nitrobenzenesulfonates and benzenesulfonates.

The compounds V can be prepared by generally known processes for olefin synthesis (Houben-Weyl-Müller, Methoden der organischen Chemie, Georg Thieme Verlag, Stuttgart, 1972, Vol. V, 1b).

The compounds of the formula IV are obtained, for example, by reacting a compound of the formula VI with a compound of the formula III.

The Examples which follow illustrate the preparation of the active ingredients.

I. PREPARATION OF THE STARTING MATERIALS

Method A 4.2 g of sodium hydroxide in 30 ml of water are added to a solution of 35 g of 2-chlorobenzaldehyde in 300 ml of methanol. The reaction mixture is cooled to 10° C. and 36 g of 2-(2-formylethyl)-1,3-dioxane are added rapidly, the temperature of the solution increasing to 30°–40° C. Stirring is carried out for 10 hours at 40° C., after which 200 ml of water are added to the colorless reaction solution and the resulting emulsion is extracted by shaking with methyl tert-butyl ether. The organic phase is separated off, dried over sodium sulfate and evaporated down. After filtration of the remaining residue over a silica gel column (1:9 ethyl acetate/n-hexane), 52 g (78%) of E/Z-2-(1,3-dioxan-2-ylmethyl)-3-(2-chlorophenyl)-propenal are obtained.

Method B 52 g of E/Z-2-(1,3-dioxan-2-ylmethyl)-3-(2-chlorophenyl)-propenal are dissolved in 300 ml of methanol, and 2.21 ml of concentrated sodium hydroxide solution are added. The reaction solution is stirred at 0° C. while 14.3 g of hydrogen peroxide (about 50% strength by weight) are slowly added dropwise, the internal temperature not exceeding 30° C. When the addition has ended, stirring is continued for 6 hours at room temperature (20° C.) and 2.35 g of sodium borohydride, dissolved in a little 10% strength sodium hydroxide solution, are then added. After the reaction mixture has been stirred for 18 hours at room temperature, 200 ml of water are added to the solution and the resulting emulsion is extracted by shaking with methylene chloride. The organic phase isolated is then dried over sodium sulfate and evaporated down, and the remaining residue is recrystallized from isopropanol. 49 g (88%) of cis-2-hydroxymethyl-2-(1,3-dioxan-2-ylmethyl)-3-(2-chlorophenyl)-oxirane of melting point 79° C. are obtained.

Method C 37.5 g of 4-methylbenzenesulfonyl chloride are added to a solution of 49 g of cis-2-(1,3-dioxan-2-yl-methyl)-3-(2-chlorophenyl)-oxirane in 200 ml of dichloromethane and 53 g of triethylamine at room temperature. After 24 hours, the reaction mixture is washed with aqueous sodium bicarbonate solution and water, dried over sodium sulfate and evaporated down under reduced pressure. The residue gives 59.5 g (80%) of cis-2-(4-methylphenylsulfonyloxymethyl)-2-(1,3-dioxan-2-ylmethyl)-3-(2-chlorophenyl)-oxirane, which is then further treated with triazole according to the Example below.

Method D 13.7 g of 4,4-dimethylpentanal are added dropwise in the course of 3 hours to a solution of 0.6 g of sodium hydroxide and 16.9 g of 4-chlorobenzaldehyde in 100 ml of methanol at 30° C. The reaction solution is stirred for 30 minutes at 30° C. and then brought to pH 7 with 10% strength sulfuric acid, precipitated sodium sulfate is filtered off and the filtrate is evaporated down. In the subsequent distillation of the remaining residue, 21.6 g (76%) of Z-2-(2,2-dimethylpropyl)-3-(4-chlorophenyl)-propenal are obtained under 0.4 mbar and at a distillation temperature of 117° C.

Method E 2.1 g of sodium borohydride, dissolved in a little 10% strength sodium hydroxide solution, are added to a solution of 47.3 g of Z-2-(2,2-dimethylpropyl)-3-(4-chlorophenyl)-propenal. After the reaction mixture has been stirred for 18 hours at room temperature, 200 ml of water are added to the solution and the resulting emulsion is extracted by shaking with methylene chloride. The organic phase isolated is then dried over sodium sulfate and evaporated down. 45.8 g (96%) of Z-1-(4-chlorophenyl)-2-hydroxymethyl-4,4-dimethylpent-1-ene are obtained.

Method F 42 g of 4-methylbenzenesulfonyl chloride are added to a solution of 45.8 g of Z-1-(4-chlorophenyl)-2-hydroxymethyl-4,4-dimethylpent-1-ene in 200 ml of methylene chloride and 59 g of triethylamine at room temperature. After 24 hours, the reaction mixture is washed with aqueous sodium bicarbonate solution and water, dried over sodium sulfate and evaporated down under reduced pressure. The residue gives 73.1 g (98%) of Z-1-(4-chlorophenyl)-2-(4-methylphenylsulfonyloxymethyl)-4,4-dimethylpent-1-ene.

II. PREPARATION OF THE END PRODUCTS

Example 1

5.2 g of sodium hydroxide are added to a solution of 9.4 g of 1,2,4-triazole in 100 ml of N-methylpyrrolidone and the mixture is heated at 50° C. for 30 minutes. After the reaction mixture has been cooled to room temperature, 59.5 g of cis-2-(4-methylphenylsulfonyloxymethyl)-2-(1,3-dioxan-2-ylmethyl)-3-(2-chlorophenyl)-oxirane, dissolved in 100 ml of N-methylpyrrolidone, are slowly added dropwise to the solution and stirring is carried out for 12 hours at room temperature. Thereafter, 200 ml of water are added and the mixture is extracted several times with methyl tert-butyl ether; the organic phase is washed with water, dried over sodium sulfate and evaporated down. 36.8 g (81%) of cis-2-(1,2,4-triazol-1-ylmethyl)-2-(1,3-dioxan-2-ylmethyl)-3-(2-chlorophenyl)-oxirane of melting point 96°-111° C. (compound No. 1) are obtained by crystallization from methyl tert-butyl ether/ n-hexane.

The compounds listed in Table 1 can be prepared similarly to Example 1.

Example 2

9.2 g of sodium hydroxide are added to a solution of 16.8 g of 1,2,4-triazole in 150 ml of N-methylpyrrolidone and the mixture is heated at 50° C. for 30 minutes. After the reaction mixture has been cooled to room temperature, 73.1 g of Z-1-(4-chlorophenyl)-2-(4-methylphenylsulfonyloxymethyl)-4,4-dimethylpent-1-ene, dissolved in 100 ml of N-methylpyrrolidone, are slowly added dropwise to the solution and stirring is carried out for 12 hours at room temperature. Thereafter, 200 ml of water are added and the mixture is extracted several times with methyl tert-butyl ether, and the organic phase is washed twice with water, dried over sodium sulfate and evaporated down. The remaining residue is chromatographed over silica gel using 9:1 n-hexane/ethyl acetate to give 38 g (71%) of Z-1-(4-chlorophenyl)-2-(1,2,4-triazol-1-ylmethyl)-4,4-dimethylpent-1-ene, which can be crystallized from methyl tert-butyl ether/n-hexane (mp.: 81°-84° C., compound No. A1).

The compounds listed in Table 2 can be prepared similarly to Example 2.

TABLE 1

$$\begin{array}{c} X \\ \diagdown \\ N-CH_2-C \underset{\underset{R_1-(CH_2)_n \; (CH_2)_m-R_2}{|}}{\overset{O}{\diagup \diagdown}} CH \end{array} \quad I,$$

| Ex. | n | m | $R_1$ | $R_2$ | X | M.p./IR |
|---|---|---|---|---|---|---|
| 1 | 1 | 0 | ⟨dioxan-2-yl⟩ | 2-Cl—$C_6H_4$ | N | 96–111° C. |
| 2 | 1 | 0 | tert.-butyl | 4-Cl—$C_6H_4$ | N | 59–67° C. |
| 3 | 1 | 0 | 4-F—$C_6H_4$ | tert.-butyl | N | — |
| 4 | 1 | 0 | 4-F—$C_6H_4$ | 2-Cl—$C_6H_4$ | N | resin |
| 5 | 1 | 0 | tert.-butyl | cyclohexyl | N | 2929, 1506, 1274, 1139, 1016 cm$^{-1}$ |
| 6 | 1 | 1 | tert.-butyl | 4-Cl—$C_4H_6$ | N | 70–77° C. |
| 7 | 1 | 1 | 4-F—$C_6H_4$ | tert.-butyl | N | 75–77° C. |
| 8 | 1 | 2 | 4-F—$C_6H_4$ | 4-F—$C_6H_4$ | N | resin |
| 9 | 1 | 2 | 4-Cl—$C_6H_4$ | tert.-butyl | N | resin |
| 10 | 0 | 1 | tert.-butyl | 2-Cl—$C_6H_4$ | N | — |
| 11 | 0 | 1 | tert.-butyl | 4-Cl—$C_6H_4$ | N | — |
| 12 | 0 | 1 | tert.-butyl | 4-F—$C_6H_4$ | N | 49–52° C. |

TABLE 1-continued

Structure I: imidazole/triazole-N-CH₂-C(R₁(CH₂)ₙ)(epoxide-O-CH((CH₂)ₘ-R₂))

| Ex. | n | m | R₁ | R₂ | X | M.p./IR |
|---|---|---|---|---|---|---|
| 13 | 0 | 1 | 4-F—C₆H₄ | 2-Cl—C₆H₄ | N | — |
| 14 | 0 | 1 | 4-F—C₆H₄ | 2-Cl—C₆H₄ | CH | — |
| 15 | 0 | 1 | 4-F—C₆H₄ | 3-Cl—C₆H₄ | N | — |
| 16 | 0 | 1 | 4-F—C₆H₄ | 3-Cl—C₆H₄ | CH | — |
| 17 | 0 | 1 | 4-F—C₆H₄ | 4-Cl—C₆H₄ | N | — |
| 18 | 0 | 1 | 4-F—C₆H₄ | 4-Cl—C₆H₄ | CH | — |
| 19 | 0 | 1 | 4-F—C₆H₄ | 2,4-Cl₂—C₆H₃ | N | — |
| 20 | 0 | 1 | 4-F—C₆H₄ | 2,4-Cl₂—C₆H₃ | CH | — |
| 21 | 0 | 1 | 4-F—C₆H₄ | 2-CF₃—C₆H₄ | N | — |
| 22 | 0 | 1 | 4-F—C₆H₄ | 2-CF₃—C₆H₄ | CH | — |
| 23 | 0 | 1 | 4-F—C₆H₄ | 4-CF₃—C₆H₄ | CH | — |
| 24 | 0 | 1 | 4-F—C₆H₄ | 4-CF₃—C₆H₄ | N | — |
| 25 | 0 | 1 | 4-Cl—C₆H₄ | 2-Cl—C₆H₄ | N | — |
| 26 | 0 | 1 | 4-Cl—C₆H₄ | 2-Cl—C₆H₄ | CH | — |
| 27 | 0 | 1 | 4-Cl—C₆H₄ | 4-Cl—C₆H₄ | N | — |
| 28 | 0 | 1 | 4-Cl—C₆H₄ | 4-Cl—C₆H₄ | CH | — |
| 29 | 0 | 1 | 4-Cl—C₆H₄ | 4-F—C₆H₄ | N | — |
| 30 | 0 | 1 | 4-Cl—C₆H₄ | 4-F—C₆H₄ | CH | — |
| 31 | 0 | 1 | 4-Cl—C₆H₄ | 2-F—C₆H₄ | N | — |
| 32 | 0 | 1 | 4-Cl—C₆H₄ | 2,4-Cl₂—C₆H₃ | N | — |
| 33 | 0 | 1 | 4-Cl—C₆H₄ | 2,4-Cl₂—C₆H₃ | CH | — |
| 34 | 0 | 1 | 2,4-Cl₂—C₆H₃ | 2-Cl—C₆H₄ | N | — |
| 35 | 0 | 1 | 2,4-Cl₂—C₆H₃ | 2-Cl—C₆H₄ | N | — |
| 36 | 0 | 1 | 2,4-Cl₂—C₆H₃ | 4-F—C₆H₄ | N | — |
| 37 | 0 | 1 | 2,4-Cl₂—C₆H₃ | 4-F—C₆H₄ | CH | — |
| 38 | 0 | 1 | 2,4-Cl₂—C₆H₃ | 2,4-Cl₂—C₆H₃ | N | — |
| 39 | 0 | 2 | 4-F—C₆H₄ | 4-Cl—C₆H₄ | N | — |
| 40 | 0 | 2 | 4-F—C₆H₄ | 3-Cl—C₆H₄ | N | — |
| 41 | 0 | 2 | 4-F—C₆H₄ | 2-Cl—C₆H₄ | N | — |
| 42 | 0 | 2 | 4-Cl—C₆H₄ | 4-Cl—C₆H₄ | N | — |
| 43 | 0 | 2 | 4-Cl—C₆H₄ | 2-Cl—C₆H₄ | N | — |
| 44 | 0 | 2 | 4-Cl—C₆H₄ | 4-F—C₆H₄ | N | — |
| 45 | 0 | 2 | 4-Cl—C₆H₄ | 2-F—C₆H₄ | N | — |
| 46 | 0 | 2 | 4-Cl—C₆H₄ | 2-OCH₃—C₆H₄ | N | — |
| 47 | 0 | 2 | 4-OCH₃—C₆H₄ | 4-Cl—C₆H₄ | N | — |
| 48 | 0 | 2 | 4-OCH₃—C₆H₄ | 2-F—C₆H₄ | N | — |
| 49 | 0 | 2 | tert.butyl | cyclohexyl | N | — |
| 50 | 0 | 2 | 4-Cl—C₆H₄ | cyclohexyl | N | — |
| 51 | 0 | 2 | 4-Cl—C₆H₄ | cyclohexyl | N | — |
| 52 | 0 | 2 | 4-F—C₆H₄ | cyclopentyl | N | — |
| 53 | 2 | 2 | 2-Cl—C₆H₄ | 2-Cl—C₆H₄ | N | — |
| 54 | 2 | 2 | 4-Cl—C₆H₄ | cyclohexyl | N | — |
| 55 | 1 | 3 | 4-F—C₆H₄ | 4-F—C₆H₄ | N | — |
| 56 | 1 | 4 | 4-F—C₆H₄ | 2-F—C₆H₄ | N | — |
| 57 | 2 | 4 | 2,4-Cl₂—C₆H₃ | 2-Cl—C₆H₄ | N | — |
| 58 | 3 | 3 | 2-Cl—C₆H₄ | 3-Cl—C₆H₄ | N | — |
| 59 | 0 | 5 | 2-F—C₆H₄ | 4-CH₃—C₆H₄ | N | — |
| 60 | 2 | 5 | 4-F—C₆H₄ | 4-F—C₆H₄ | N | — |
| 61 | 1 | 0 | C₆H₅ | 2-Cl—C₆H₄ | N | — |
| 62 | 0 | 1 | 2-Cl—C₆H₄ | C₆H₅ | N | — |

TABLE 2

Structure I: imidazole/triazole-N-CH₂-C(R₁(CH₂)ₙ)=CH-(CH₂)ₘ-R₂

| Ex. | n | m | R₁ | R₂ | X | M.p./IR | Isomer |
|---|---|---|---|---|---|---|---|
| A1 | 1 | 0 | tert.-butyl | 4-Cl—C₆H₄ | N | 81–84° C. | cis |
| A2 | 1 | 0 | tert.-butyl | 4-Cl—C₆H₄ | CH | — | — |
| A3 | 1 | 0 | tert.-butyl | 4-F—C₆H₄ | N | — | — |
| A4 | 1 | 0 | tert.-butyl | cyclohexyl | N | — | — |
| A5 | 1 | 0 | tert.-butyl | cyclohexyl | CH | — | — |
| A6 | 1 | 0 | 4-F—C₆H₄ | tert.-butyl | N | — | — |
| A7 | 1 | 0 | 4-F—C₆H₄ | tert.-butyl | CH | — | — |
| A8 | 1 | 0 | 4-Cl—C₆H₄ | tert.-butyl | N | — | — |
| A9 | 1 | 1 | 4-F—C₆H₄ | tert.-butyl | N | — | — |
| A10 | 1 | 1 | 4-F—C₆H₄ | tert.-butyl | CH | — | — |
| A11 | 1 | 2 | 4-F—C₆H₄ | 4-F—C₆H₄ | N | — | — |
| A12 | 1 | 2 | 4-F—C₆H₄ | 4-F—C₆H₄ | CH | — | — |
| A13 | 1 | 2 | 4-Cl—C₆H₄ | tert.butyl | N | resin | E/Z = 55:45 |
| A14 | 0 | 1 | tert.-butyl | 2-Cl—C₆H₄ | N | — | — |
| A15 | 0 | 1 | tert.-butyl | 2-Cl—C₆H₄ | CH | — | — |
| A16 | 0 | 1 | 4-F—C₆H₄ | 2-Cl—C₆H₄ | N | — | — |
| A17 | 0 | 1 | 4-F—C₆H₄ | 2-Cl—C₆H₄ | CH | — | — |
| A18 | 0 | 1 | 4-Cl—C₆H₄ | 2-Cl—C₆H₄ | N | — | — |
| A19 | 0 | 1 | 4-Cl—C₆H₄ | 2-Cl—C₆H₄ | CH | — | — |
| A20 | 0 | 1 | 2,4-Cl₂—C₆H₃ | 2-Cl—C₆H₄ | N | — | — |
| A21 | 0 | 1 | 2,4-Cl₂—C₆H₃ | 2-Cl—C₆H₄ | CH | — | — |
| A22 | 0 | 1 | 2,4-Cl₂—C₆H₃ | 4-F—C₆H₄ | N | — | — |
| A23 | 0 | 2 | 4-F—C₆H₄ | 4-Cl—C₆H₄ | N | — | — |
| A24 | 0 | 2 | 4-F—C₆H₄ | 4-Cl—C₆H₄ | CH | — | — |
| A25 | 0 | 2 | 4-F—C₆H₄ | 2-Cl—C₆H₄ | N | — | — |
| A26 | 0 | 2 | 4-OCH₃—C₆H₄ | 4-Cl—C₆H₄ | N | — | — |
| A27 | 0 | 2 | 4-OCH₃—C₆H₄ | 4-Cl—C₆H₄ | CH | — | — |
| A28 | 0 | 2 | tert.-butyl | cyclohexyl | N | — | — |
| A29 | 0 | 2 | 4-Cl—C₆H₄ | cyclohexyl | N | — | — |
| A30 | 0 | 2 | 4-Cl—C₆H₄ | cyclohexyl | CH | — | — |
| A31 | 0 | 2 | 4-F—C₆H₄ | cyclohexyl | N | — | — |
| A32 | 0 | 1 | C₆H₅ | 2-Cl—C₆H₄ | N | — | — |
| A33 | 0 | 1 | C₆H₅ | 2-Cl—C₆H₄ | CH | — | — |
| A34 | 1 | 0 | 2-Cl—C₆H₄ | C₆H₅ | N | — | — |
| A35 | 1 | 0 | 2-Cl—C₆H₄ | C₆H₅ | CH | — | — |
| A36 | 2 | 2 | 2-Cl—C₆H₄ | 2-Cl—C₆H₄ | N | — | — |
| A37 | 2 | 2 | 2-Cl—C₆H₄ | 2-Cl—C₆H₄ | CH | — | — |
| A38 | 1 | 3 | 4-F—C₆H₄ | 4-F—C₆H₄ | N | — | — |

TABLE 2-continued $$\begin{array}{c} X \\ \diagup \\ N-CH_2-C=CH-(CH_2)_m-R_2 \\ N \diagdown \diagup \quad | \\ R_1-(CH_2)_n \end{array}$$

| Ex. | n | m | R$_1$ | R$_2$ | X | M.p./IR | Isomer |
|-----|---|---|-------|-------|---|---------|--------|
| A39 | 1 | 3 | 4-F—C$_6$H$_4$ | 4-F—C$_6$H$_4$ | CH | — | — |
| A40 | 1 | 4 | 4-F—C$_6$H$_4$ | 2-F—C$_6$H$_4$ | N | — | — |
| A41 | 1 | 4 | 4-F—C$_6$H$_4$ | 2-F—C$_6$H$_4$ | CH | — | — |
| A42 | 2 | 4 | 2,4-Cl$_2$—C$_6$H$_3$ | 2-Cl—C$_6$H$_4$ | N | — | — |
| A43 | 3 | 3 | 2-Cl—C$_6$H$_4$ | 3-Cl—C$_6$H$_4$ | N | — | — |
| A44 | 3 | 3 | 2-Cl—C$_6$H$_4$ | 3-Cl—C$_6$H$_4$ | CH | — | — |
| A45 | 0 | 5 | 2-F—C$_6$H$_4$ | 4-CH$_3$—C$_6$H$_4$ | N | — | — |
| A46 | 0 | 5 | 2-F—C$_6$H$_4$ | 4-CH$_3$—C$_6$H$_4$ | CH | — | — |
| A47 | 2 | 5 | 4-F—C$_6$H$_4$ | 4-F—C$_6$H$_4$ | N | — | — |
| A48 | 2 | 5 | 4-F—C$_6$H$_4$ | 4-F—C$_6$H$_4$ | CH | — | — |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 6 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 7 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 4 is intimately mixed with 97 parts by weight of particulate kaolin. A dust is obtained containing 3% by weight of the active ingredient.

VII. 30 parts by weight of compound no. 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 7 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 8 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene, DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, cis-2-(1,2,4-triazolylmethyl)-2-(tert-butyl)-3-(4-chlorophenyl)-oxirane (A) disclosed in DE 3 218 130.2 was employed.

USE EXAMPLE 1

Action on Wheat Brown Rust

Leaves of pot-grown wheat seedlings of the "Frühgold" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 2, 6, 7 and 8 have, when applied as 0.025 wt % spray liquors, a better fungicidal action (97%) than prior art comparative agent A (60%).

USE EXAMPLE 2

Action on *Pyrenophora Teres*

Leaves of pot-grown barley seedlings of the "Igri" variety were sprayed to runoff at the 2-leaf stage with aqueous suspensions containing (dry basis) 80% of active ingredient and 20% of emulsifier. After 24 hours the plants were inoculated with a spore suspension of *Pyrenophora teres* and set up for 48 hours in a high-humidity climatic cabinet at 18° C. The plants were then cultivated for a further 5 days in the greenhouse at 20° to 22° C. and a relative humidity of 70%. The extent of the spread of the symptoms was then assessed.

The results show that active ingredients 2, 4, 5, 7 and 8 have a good fungicidal action (90%) when applied as 0.05% spray liquors.

We claim:

1. A member selected from the group consisting of an azolylmethyloxirane of the formula:

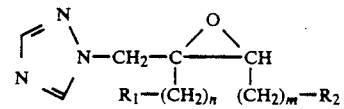

wherein $R_1$ and $R_2$ are t-butyl, naphthyl, biphenyl, dioxanyl or phenyl, each of these radicals being unsubstituted or substituted by halogen, nitro, phenoxy, alkyl, alkoxy, amino or haloalkyl, where each alkyl radical contains 1 to 4 carbon atoms, m and n are each an integer of from 1 to 5 or 0, with the proviso that m+n is 1 or more and when $R_1$ or $R_2$ is t-butyl, the corresponding m or n is at least 1, and their plant-tolerated acid addition salts and metal complexes.

2. A member selected from the group consisting of an azolylmethyloxirane of the formula:

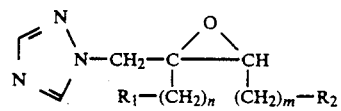

wherein $R_1$ and $R_2$ are each independently t-butyl, naphthyl, biphenyl, dioxanyl or phenyl, each of these radicals being unsubstituted or substituted by halogen, nitro, phenoxy, alkyl, alkoxy, amino or haloalkyl, wherein each alkyl radical contains 1 to 4 carbon atoms; m and n are each an integer of from 1 to 5 or 0, with the proviso that m+n is at least 1 and that when either $R_1$ or $R_2$ is t-butyl, the remaining radical cannot be t-butyl and subscript m or n of the remaining radical cannot be 0, and the m or n value corresponding to the value of $R_1$ or $R_2$ as t-butyl must be at least 1, and their plant-tolerated acid addition salts and metal complexes.

3. A compound as set forth in claim 1, where $R_1$ is tert-butyl, $R_2$ is 4-chlorophenyl, n is 1, and m is 0.

4. A compound as set forth in claim 1, where $R_1$ is 4-fluorophenyl, $R_2$ is tert-butyl, n is 1, and m is 1.

5. A compound as set forth in claim 1, where $R_1$ is tert-butyl, $R_2$ is 4-chlorophenyl, n is 1, and m is 1.

6. A fungicidal composition, comprising:
a fungicidally effective amount of a member selected from the group consisting of an azolylmethyloxirane of the formula:

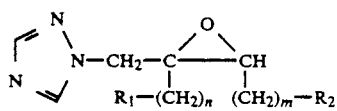

wherein $R_1$ and $R_2$ are each independently t-butyl, naphthyl, biphenyl, dioxanyl or phenyl, each of these radicals being unsubstituted or substituted by halogen, nitro, phenoxy, alkyl, alkoxy, amino or haloalkyl, wherein each alkyl radical is of 1 to 4 carbon atoms; m and n are each an integer of from 1 to 5 or 0, with the proviso that m+n is at least 1 or more and that when either $R_1$ or $R_2$ is t-butyl, the corresponding value of m or n cannot be 0, and their plant-tolerated acid addition salts and metal complexes thereof, in combination with an inert carrier.

7. A method for combating fungi, comprising:
treating soil, plants or seed threatened by fungus attack with a fungicidally effective amount of a member selected from the group consisting of an azolylmethyloxirane of the formula:

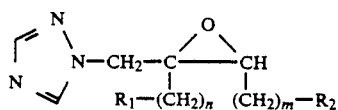

wherein $R_1$ and $R_2$ are each independently t-butyl, naphthyl, biphenyl, dioxanyl or phenyl, each of these radicals being unsubstituted or substituted by halogen, nitro, phenoxy, alkyl, alkoxy, amino or haloalkyl, wherein each alkyl radical is of 1 to 4 carbon atoms; m and n are each an integer of from 1 to 5 or 0, with the proviso that m+n is at least 1 and that when either $R_1$ or $R_2$ is t-butyl, the corresponding value of m or n cannot be 0, and their plant-tolerated acid addition salts and metal complexes.

8. The composition of claim 6 which contains from 0.1–95 wt. % of active fungicidal ingredient.

9. The method of claim 7, wherein from 0.02–3 kg of active fungicidal ingredient is applied per hectare of soil.

10. An azolylmethyloxirane of claim 2, wherein substituents $R_1$ and $R_2$ are each tert-butyl, 1-naphthyl, 2-naphthyl, p-biphenyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tert-butoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl, 4-trifluoromethylphenyl, 1,3-dioxan-2-yl or 1,4-dioxan-1-yl provided that both of $R_1$ and $R_2$ cannot be t-butyl.

* * * * *